(12) United States Patent
Lee et al.

(10) Patent No.: US 10,296,810 B2
(45) Date of Patent: May 21, 2019

(54) APPARATUS AND METHOD FOR DETERMINING LESION SIMILARITY OF MEDICAL IMAGE

(71) Applicant: Samsung Electronics Co., Ltd., Suwon-si, Gyeonggi-do (KR)

(72) Inventors: Ki-Young Lee, Suwon-si (KR); Yeong-Kyeong Seong, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 11 days.

(21) Appl. No.: 15/103,684

(22) PCT Filed: Jun. 12, 2014

(86) PCT No.: PCT/KR2014/005178
§ 371 (c)(1),
(2) Date: Jun. 10, 2016

(87) PCT Pub. No.: WO2015/099249
PCT Pub. Date: Jul. 2, 2015

(65) Prior Publication Data
US 2016/0314375 A1     Oct. 27, 2016

(30) Foreign Application Priority Data
Dec. 27, 2013 (KR) .......... 10-2013-0166118

(51) Int. Cl.
*G06K 9/00* (2006.01)
*G06K 9/62* (2006.01)
(Continued)

(52) U.S. Cl.
CPC ............ *G06K 9/6215* (2013.01); *A61B 5/103* (2013.01); *A61B 5/7271* (2013.01);
(Continued)

(58) Field of Classification Search
None
See application file for complete search history.

(56) References Cited

U.S. PATENT DOCUMENTS 7,814,107 B1   10/2010   Thirumalai et al.
8,081,822 B1   12/2011   Bell
(Continued)

FOREIGN PATENT DOCUMENTS

KR   10-2007-0073754 A   7/2007
KR   10-2009-0010555 A   1/2009
(Continued)

OTHER PUBLICATIONS

Song Yang et al: "Similarity Guided Feature Labeling for Lesion Detection", Sep. 22, 2013, Network and Parallel Computing; [Lecture Notes in Computer Science; Lect.Notes Computer], Springer International Publishing, CHAM, pp. 284-291, XP047041952.
(Continued)

*Primary Examiner* — Randolph I Chu
(74) *Attorney, Agent, or Firm* — Jefferson IP Law, LLP (57) ABSTRACT

Disclosed are an apparatus and a method for determining lesion similarity of a medical image. The apparatus for determining lesion similarity according to one aspect of the present invention may comprise: an image input unit for receiving a reference image comprising a reference lesion area, and a target image comprising a target lesion area; and a similarity determination unit for determining similarity of the reference lesion area and the target lesion area by applying an advantage weight, which increases as getting closer to the center of the reference lesion area, to pixels included in a first area of the reference lesion area, and a penalty weight, which increases as getting farther away from the reference lesion area, to pixels included in a second area of the target lesion area.

17 Claims, 6 Drawing Sheets

(51) Int. Cl.
*A61B 5/103* (2006.01)
*G06T 7/00* (2017.01)
*A61B 5/00* (2006.01)

(52) U.S. Cl.
CPC ........ *G06T 7/0014* (2013.01); *A61B 2505/05* (2013.01); *A61B 2576/00* (2013.01); *G06T 2207/10132* (2013.01); *G06T 2207/30096* (2013.01)

(56) References Cited

U.S. PATENT DOCUMENTS

| | | |
|---|---|---|
| 8,187,602 B2 | 5/2012 | Goto et al. |
| 8,620,930 B2 | 12/2013 | Gulhane et al. |
| 2004/0236225 A1 | 11/2004 | Murphy et al. |
| 2004/0247166 A1* | 12/2004 | Giger ................... G06F 19/321 382/128 |
| 2010/0329549 A1 | 12/2010 | Steinberg et al. |
| 2012/0022381 A1 | 1/2012 | Tearney et al. |
| 2012/0262453 A1* | 10/2012 | Endo .................... A61B 8/483 345/419 |
| 2013/0182901 A1* | 7/2013 | Ishida ................... G06T 7/0012 382/103 |
| 2013/0188851 A1 | 7/2013 | Miyasa et al. |
| 2014/0037051 A1 | 2/2014 | Choi et al. |

FOREIGN PATENT DOCUMENTS

| | | |
|---|---|---|
| KR | 10-1112056 B1 | 2/2012 |
| WO | 02082988 A2 | 10/2002 |
| WO | 2007144620 A2 | 12/2007 |
| WO | 2012-099314 A1 | 7/2012 |
| WO | 2012-153904 A1 | 11/2012 |

OTHER PUBLICATIONS

Muramatsu Chisako et al: "Representation of Lesion Similarity by Use of Multidimensional Scaling for Breast Masses on Mammograms", Journal of Digital Imaging, Springer-Verlag, CHAM, vol. 26. No. 4, Jan. 11, 2013, pp. 740-747, XP035346002.

Mihail Popescu et al: "Fuzzy Measures on the Gene Ontology for Gene Product Similarity" IEEE/ACMTransactionsonComputationalBiologyandBioinformatics,vol. 3,No. 3, Jul.-Sep. 2006.

* cited by examiner

APPARATUS AND METHOD FOR DETERMINING LESION SIMILARITY OF MEDICAL IMAGE

TECHNICAL FIELD

The following description relates to analysis technology of medical images, and more particularly to an apparatus and method for determining similarity of lesions in medical images.

BACKGROUND ART

Computer-aided diagnosis (CAD) systems help doctors to diagnose diseases by analyzing medical images, such as ultrasound images, and by displaying abnormal portions in the medical images based on the analysis. Such CAD systems may reduce diagnosis uncertainty caused by a human's limited ability to detect, and may also reduce doctors' heavy workload in reading each medical image.

A main task used in the analysis of medical images and in the CAD system is accurate and effective detection of lesion areas from medical images. To this end, various algorithms are used, in which algorithms mainly used for image processing or data analysis processing in other technical fields are used as a measure to evaluate detection accuracy of detected lesion areas. However, such measure may not reflect characteristics of medical images.

SUMMARY

An object of the present invention is to provide an apparatus and method for determining a lesion similarity of medical images.

In one general aspect, there is provided an apparatus for determining a lesion similarity, the apparatus including: an image input section configured to receive input of a reference image including a reference lesion area, and a target image including a target lesion area; and a similarity determiner configured to determine a similarity between the reference lesion area and the target lesion area by applying an advantage weighted value to a pixel included in a first area of the target lesion area, the advantage weighted value increasing as the pixel of the first area gets closer to a center of the reference lesion area, and by applying a penalty weighted value to a pixel included in a second area of the target lesion area, the penalty weighted value increasing as the pixel of the second area gets farther from the reference lesion area.

The first area may be an area of the target lesion area that is included in the reference lesion area, and the second area may be an area of the target lesion area that is not included in the reference lesion area.

The advantage weighted value and the penalty weighted value may be increased linearly or exponentially.

The similarity determiner may include: a distance map generator configured to calculate the shortest distance between each pixel of the reference image and a boundary of the reference lesion area, and to generate a first distance map representing the advantage weighted value and a second distance map representing the penalty weighted value based on the calculated shortest distance; and a similarity calculator configured to calculate the similarity between the reference lesion area and the target lesion area by using the first distance map and the second distance map.

The similarity determiner may further include a binarizer configured to binarize the reference image and the target image.

The binarizer may binarize the reference image so that each pixel inside the reference lesion area is binarized to a binary value "1", and each pixel outside the reference lesion area is binarized to a binary value "0", and the binarizer may binarize the target image so that each pixel inside the target lesion area is binarized to a binary value "1", and each pixel outside the target lesion area is binarized to a binary value "0".

The similarity calculator may calculate the similarity between the reference lesion area and the target lesion area by using $$sim = \frac{sum(DM1.*(A \& B))}{sum(DM1) + sum(DM2.*(A|B))},$$

wherein A indicates a matrix representing a binarized reference image, B indicates a matrix representing a binarized target image, DM1 indicates a matrix representing the first distance map, and DM2 indicates a matrix representing the second distance map.

In another general aspect, there is provided a method of determining a lesion similarity, the method including: receiving input of a reference image including a reference lesion area, and a target image including a target lesion area; and determining a similarity between the reference lesion area and the target lesion area by applying an advantage weighted value to a pixel included in a first area of the target lesion area, the advantage weighted value increasing as the pixel of the first area gets closer to a center of the reference lesion area, and by applying a penalty weighted value to a pixel included in a second area of the target lesion area, the penalty weighted value increasing as the pixel of the second area gets farther from the reference lesion area.

The first area may be an area of the target lesion area that is included in the reference lesion area, and the second area may be an area of the target lesion area that is not included in the reference lesion area.

The advantage weighted value and the penalty weighted value may be increased linearly or exponentially.

The determining of the similarity may include: calculating the shortest distance between each pixel of the reference image and a boundary of the reference lesion area, and generating a first distance map representing the advantage weighted value and a second distance map representing the penalty weighted value based on the calculated shortest distance; and calculating the similarity between the reference lesion area and the target lesion area by using the first distance map and the second distance map.

The determining of the similarity may further include binarizing the reference image and the target image.

The binarizing may include binarizing the reference image so that each pixel inside the reference lesion area is binarized to a binary value "1", and each pixel outside the reference lesion area is binarized to a binary value "0", and binarizing the target image so that each pixel inside the target lesion area is binarized to a binary value "1", and each pixel outside the target lesion area is binarized to a binary value "0".

The calculating of the similarity may include calculating the similarity between the reference lesion area and the target lesion area by using $$sim = \frac{sum(DM1.*(A\ \&\ B))}{sum(DM1) + sum(DM2.*(A\,|\,B))},$$

wherein A indicates a matrix representing a binarized reference image, B indicates a matrix representing a binarized target image, DM1 indicates a matrix representing the first distance map, and DM2 indicates a matrix representing the second distance map.

A similarity may be determined more accurately and effectively by comparing a lesion area detected by a medical professional with a lesion area detected by the CAD system, in which a higher advantage weighted value is applied to a portion closer to the center of the lesion area detected by a medical professional, and a penalty weighted value is applied to a portion farther from the center of the lesion area detected by a medical professional.

DETAILED DESCRIPTION

The invention will be described more fully hereinafter with reference to the accompanying drawings, in which exemplary embodiments of the invention are shown. In the following description, a detailed description of known functions and configurations incorporated herein will be omitted when it may obscure the subject matter of the present invention. Further, the terms used throughout this specification are defined in consideration of the functions in the exemplary embodiments, and can be varied according to a purpose of a user or manager, or precedent and so on. Therefore, definitions of the terms should be made on the basis of the overall context.

Figure 1:
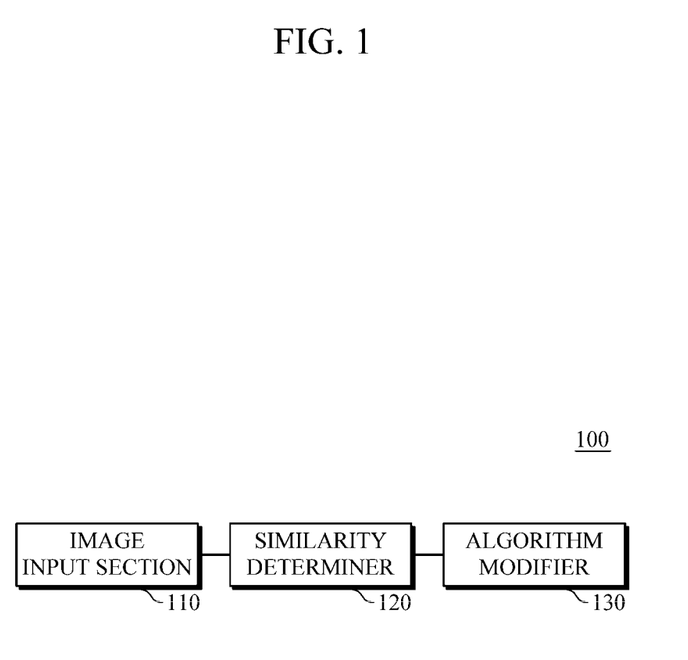
FIG. 1 is a diagram illustrating an apparatus for determining a lesion similarity according to an exemplary embodiment.

FIG. 1 is a diagram illustrating an apparatus for determining a lesion similarity according to an exemplary embodiment.

Referring to FIG. 1, the apparatus 100 for determining a lesion similarity includes an image input section 110, a similarity determiner 120, and an algorithm modifier 130.

The image input section 110 may receive input of a reference image and a target image, in which the reference image is an image that is used as a reference for the determination of a lesion similarity, and the target image is an image that is a target for determination of a lesion similarity. In the exemplary embodiment, the reference image may be an image of a lesion area which is detected by a medical professional from a medical image, and the target image may be an image of a lesion area which is detected by the CAD system from the medical image. However, the reference image and the target image are not limited thereto.

Hereinafter, a lesion area detected by the medical professional will be referred to as a reference lesion area, and a lesion area detected by the CAD system will be referred to as a target lesion area.

As described above, the image input section 110 may separately receive input of the reference image including the reference lesion area, and the target image including the target lesion area, but may also receive one image in which the reference lesion area and the target lesion area are included.

The similarity determiner 120 may divide the target lesion area into a first area, which is included in the reference lesion area, and a second area, which is not included in the reference lesion area, and may determine a similarity between the reference lesion area and the target lesion area by applying an advantage weighted value to each pixel included in the first area and by applying a penalty weighted value to each pixel included in the second area. In this case, the advantage weighted value is a weighted value applied to increase a similarity, and the penalty weighted value is a weighted value applied to decrease a similarity.

In general, a lesion area detected by a medical professional from a medical image may not be exactly the same as a lesion area detected by the CAD system from the same medical image. In order to determine a similarity between the reference lesion area detected by the medical professional and the lesion area detected by the CAD system, the similarity determiner 120 compares the reference lesion area detected by the medical professional with the target lesion area detected by the CAD system, and divides the target lesion area into the first area, which is included in the reference lesion area, and the second area, which is not included in the reference lesion area. Further, the similarity determiner 120 may determine a similarity between the reference lesion area and the target lesion area by applying different weighted values to the first area and the second area.

In the exemplary embodiment, the advantage weighted value applied to each pixel of the first area and the penalty weighted value applied to each pixel of the second area may increase with the increased shortest distance between each pixel and the boundary of the reference lesion area. That is, as each pixel of the first area gets farther from the boundary of the reference lesion area, i.e., closer to the center of the reference lesion area, a higher advantage weighted value is applied, and as each pixel of the second area gets farther from the boundary of the reference lesion area, i.e., farther from the center of the reference lesion area, a higher penalty weighted value is applied.

The advantage weighted value applied to each pixel of the first area and the penalty weighted value applied to each pixel of the second area may be increased either linearly or exponentially depending on the shortest distance between each pixel and the boundary of the reference lesion area, but are not limited thereto.

The similarity determiner 120 will be described in detail later with reference to FIG. 2.

Based on a result of the similarity determination, the algorithm modifier 130 may modify a lesion segmentation algorithm that has detected the target lesion area. For example, by using the result of similarity determination, the algorithm modifier 130 may adjust a parameter of the lesion segmentation algorithm that has detected the target lesion area.

The algorithm modifier 130 is not an essential component of the apparatus 100 for determining a lesion similarity, such that the algorithm modifier 130 may be omitted according to circumstances.

Hereinafter, the similarity determiner 120 will be described in detail below with reference to FIG. 2.

Figure 2:
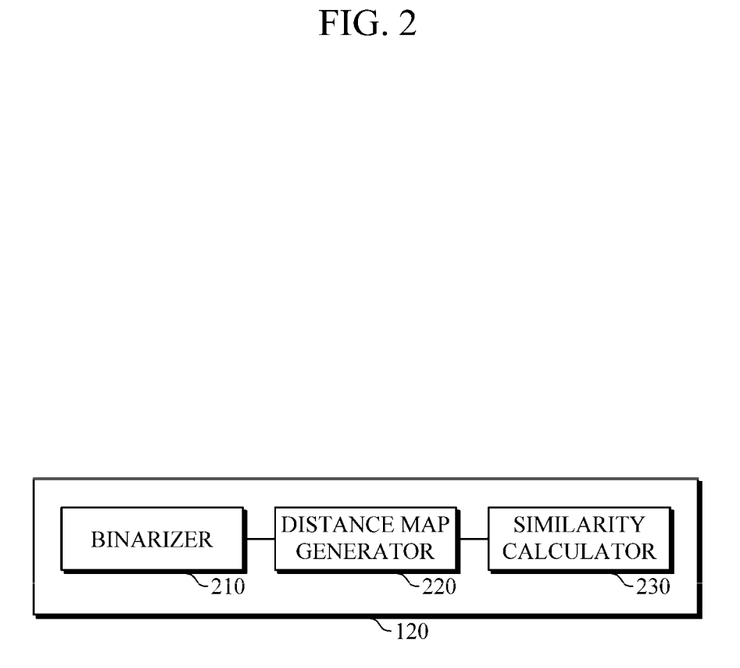
FIG. 2 is a diagram illustrating in detail a similarity determiner 120 illustrated in FIG. 1.

FIG. 2 is a diagram illustrating in detail a similarity determiner 120 illustrated in FIG. 1.

Referring to FIG. 2, the similarity determiner 120 includes a binarizer 210, a distance map generator 220, and a similarity calculator 230.

The binarizer 210 may binarize a reference image and a target image that are input through the image input section 110. In the exemplary embodiment, the binarizer 210 may binarize the reference image so that a portion inside the reference lesion area may be binarized to a binary value "1" and a portion outside the reference lesion area may be binarized to a binary value "0". Further, the binarizer 210 may binarize the target image so that a portion inside the target lesion area may be binarized to a binary value "1" and a portion outside the target lesion area may be binarized to a binary value "0".

The distance map generator 220 may generate a first distance map and a second distance map by using the binarized reference image, in which the first distance map refers to an advantage weighted value to be applied to each pixel of the first area and the second distance map refers to a penalty weighted value to be applied to each pixel of the second area.

In the exemplary embodiment, the distance map generator 220 may calculate the shortest distance between each pixel of the reference image and the boundary of the reference lesion area, and may generate the first distance map and the second distance map based on the calculation. For example, the distance map generator 220 may generate the first distance map based on the shortest distance between each pixel inside the reference lesion area and the boundary of the reference lesion area, and may generate the second distance map based on the shortest distance between each pixel outside the reference lesion area and the boundary of the reference lesion area.

The distance map generator 132 may generate the first distance map and the second distance map so that the first distance map and the second distance map may have values increasing linearly or exponentially depending on the shortest distance between each pixel and the boundary of the reference lesion area, which is merely exemplary, and generation of the distance map is not limited thereto.

The similarity calculator 230 may calculate a similarity between the reference lesion area and the target lesion area by applying an advantage weighted value to the binary value of each pixel of the first area based on the first distance map, and by applying a penalty weighted value to a binary value of each pixel of the second area based on the second distance map.

In the exemplary embodiment, the similarity calculator 230 may calculate the similarity between the reference lesion area and the target lesion area by using the following Equation 1.

$$sim = \frac{sum(DM1.*(A \& B))}{sum(DM1) + sum(DM2.*(A|B))},$$ [Equation 1]

wherein A indicates a matrix representing a binarized reference image, B indicates a matrix representing a binarized target image, DM1 indicates a matrix representing the first distance map, and DM2 indicates a matrix representing the second distance map.

Figure 3:
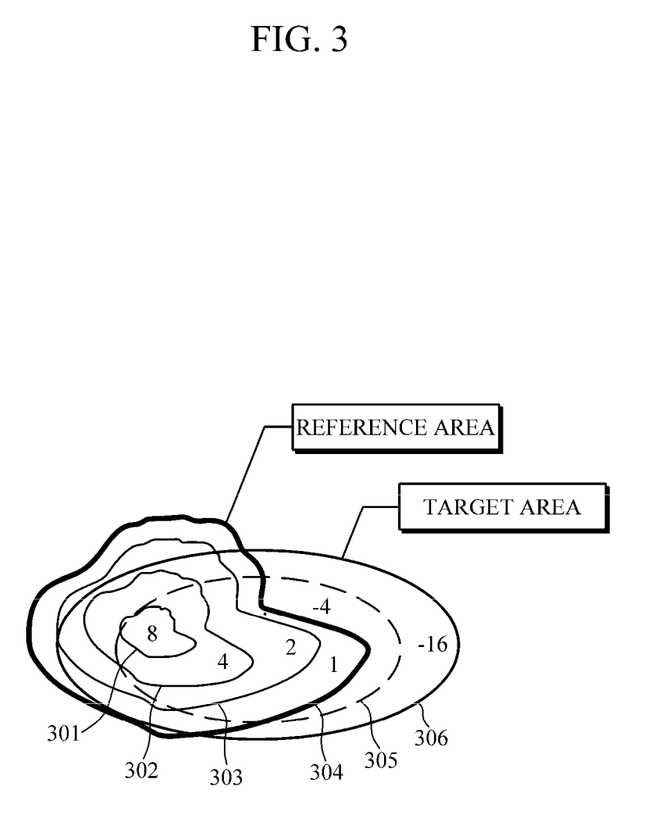
FIG. 3 is a block diagram explaining a method of determining a lesion similarity according to an exemplary embodiment.

FIG. 3 is a block diagram explaining a method of determining a lesion similarity according to an exemplary embodiment, which illustrates an example of a weighted value increasing exponentially depending on the distance from the boundary of the reference lesion area.

When determining the reference lesion area and the target lesion area, weighted values are applied differently to the inside and outside of the reference lesion area. In this case, a weighted value applied to each pixel is increased as each pixel is farther from the boundary of the reference lesion area.

Referring to FIG. 3, for the inside of the reference lesion area, a weighted value "8" may be applied to area 1 301 which is the center of the reference lesion area, a weighted value "4" may be applied to area 2 302, a weighted value "2" may be applied to area 3 303, and a weighted value "1" may be applied to area 4 304 which is adjacent to the boundary of the reference lesion area. For the outside of the reference lesion area, a weighted value "−4" may be applied to area 5 305 which is adjacent to the boundary of the reference lesion area, and a weighted value "−16" may be applied to area 6 306, in which a "minus (−)" weighted value may refer to a penalty weighted value.

As described above, a similarity between the target lesion area and the reference lesion area is increased as the target lesion area includes the central portion of the reference lesion area. By contrast, a similarity between the target lesion area and the reference lesion area is reduced as the target lesion area includes a portion farther from the boundary of the reference lesion area or includes many portions that are not included in the reference lesion area.

Figure 4:
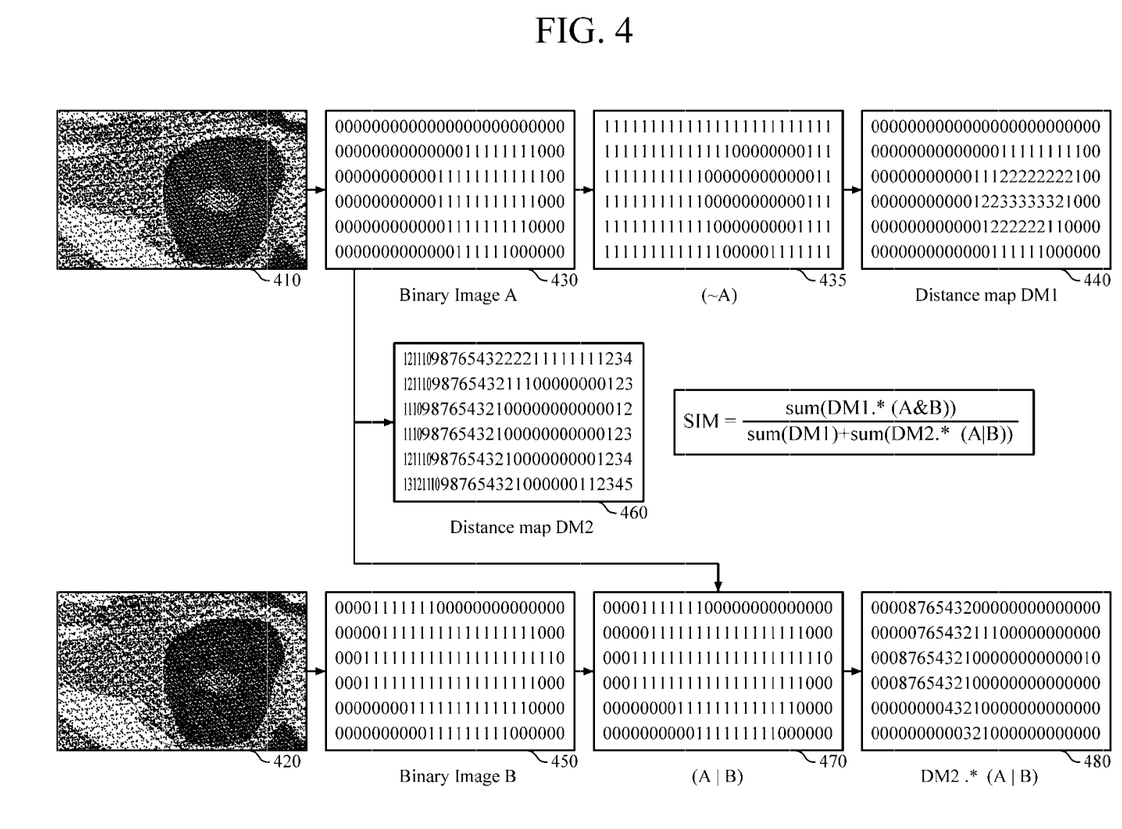
FIG. 4 is a diagram illustrating determination of a lesion similarity according to an exemplary embodiment.

FIG. 4 is a diagram illustrating determination of a lesion similarity according to an exemplary embodiment, in which for convenience of explanation, binarized images 430, 435, 450, and 470 and distance maps 440 and 460 are illustrated as a matrix.

Referring to FIGS. 1, 2, and 4, once a reference image 410 and a target image 420 are input from a user through the image input section 110, the binarizer 210 binarizes the reference image 410 in such a manner that, based on the boundary of the reference lesion area, a portion inside the reference lesion area may be binarized to a binary value "1", and a portion outside the reference lesion area may be binarized to a binary value "0", so as to generate binarized image A 430. Further, the binarizer 210 may binarize the target image 420 in such a manner that, based on the boundary of the target lesion area, a portion inside the target lesion area may be binarized to a binary value "1", and a portion outside the target lesion area may be binarized to a binary value "0", so as to generate binarized image B 450.

Based on the binarized image A 430, the distance map generator 220 may generate the distance maps 440 and 460 depending on the shortest distance between each pixel of the binarized image A 430 and the boundary of the reference lesion area. For example, the distance map generator 220 generates a reversed image 435 by switching the binary value of the binarized image A 430, and may generate the first distance map DM1 440 by using the reversed image 435. Further, the distance map generator 220 may generate the second distance map DM2 460 by using the binarized image A 430.

The similarity calculator 230 may calculate a similarity between the reference lesion area and the target lesion area by applying an advantage weighted value to a binary value of each pixel of the first area based on the first distance map DM1 440, and by applying a penalty weighted value to a binary value of each pixel of the second area based on the second distance map DM2 460.

For example, the similarity calculator 230 may calculate a lesion similarity between the reference lesion area and the target lesion area by using Equation 1.

In FIG. 4, the reference numeral 470 denotes a result of A|B, and the reference numeral 480 denotes a result of DM2. *(A|B).

Although in FIG. 4, the distance map generator 220 separately generates the first distance map DM1 440 and the second distance map DM2 460, but the distance maps are not limited thereto, and the distance map generator 220 may generate one distance map in which the first distance map DM1 440 and the second distance map DM2 460 are included.

Figure 5:
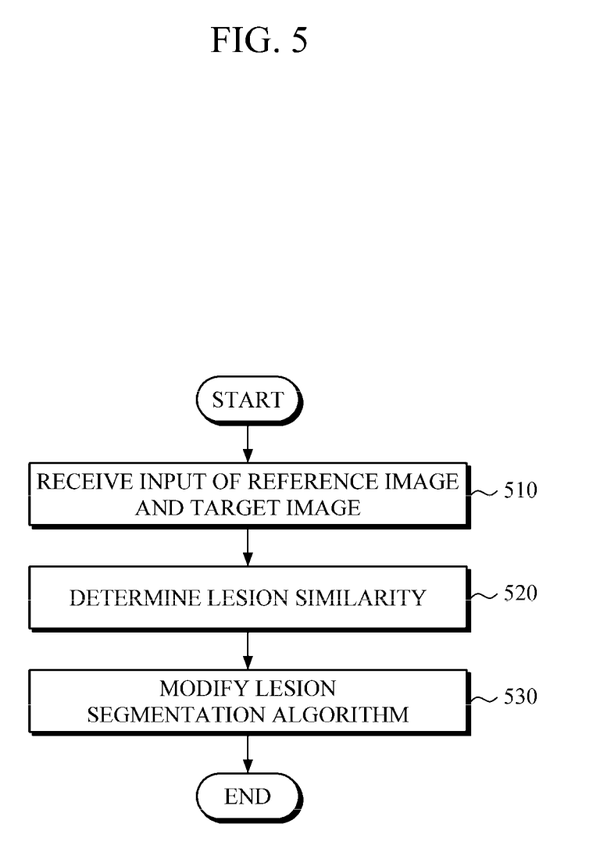
FIG. 5 is a flowchart illustrating a method of determining a lesion similarity according to an exemplary embodiment.

FIG. 5 is a flowchart illustrating a method of determining a lesion similarity according to an exemplary embodiment.

Referring to FIG. 5, the method of determining a lesion similarity includes receiving input of a reference image including a reference lesion area, and a target lesion area including a target lesion area, in 510. In this case, the reference image and the target image may be received separately, but one image that includes the reference image and the target image may also be received.

Then, the target lesion area is divided into a first area, which is included in the reference lesion area, and a second area, which is not included in the reference lesion area, and a similarity between the reference lesion area and the target lesion area is determined in 520 by applying an advantage weighted value to each pixel included in the first area and by applying a penalty weighted value to each pixel included in the second area.

In the exemplary embodiment, the advantage weighted value applied to each pixel of the first area and the penalty weighted value applied to each pixel of the second area may increase with the increased shortest distance between each pixel and the boundary of the reference lesion area. That is, as each pixel of the first area gets farther from the boundary of the reference lesion area, i.e., closer to the center of the reference lesion area, a higher advantage weighted value is applied, and as each pixel of the second area gets farther from the boundary of the reference lesion area, i.e., farther from the center of the reference lesion area, a higher penalty weighted value is applied.

Then, based on a result of the similarity determination, a lesion segmentation algorithm, which has detected the target lesion area, is modified in 530. For example, the apparatus 100 for determining a lesion similarity may adjust a parameter of the lesion segmentation algorithm that has detected the target lesion area.

Figure 6:
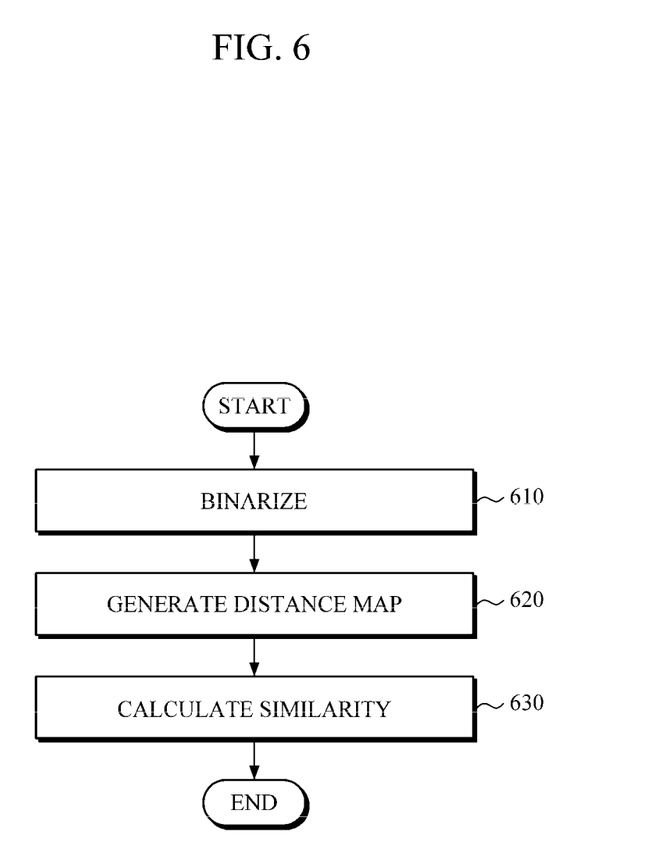
FIG. 6 is a flowchart illustrating in detail determination in 520 of a lesion similarity illustrated in FIG. 5.

FIG. 6 is a flowchart illustrating in detail determination in 520 of a lesion similarity illustrated in FIG. 5.

Referring to FIG. 6, the determination in 520 of a lesion similarity includes binarizing the reference image and the target image in 610. For example, the apparatus 100 for determining a lesion similarity binarizes the reference image in such a manner that, based on the boundary of the reference lesion area, a portion inside the reference lesion area may be binarized to a binary value "1", and a portion outside the reference lesion area may be binarized to a binary value "0". Further, the apparatus 100 for determining a lesion similarity binarizes the target image in such a manner that, based on the boundary of the target lesion area, a portion inside the target lesion area may be binarized to a binary value "1", and a portion outside the target lesion area may be binarized to a binary value "0".

Then, by using the binarized reference image, the first distance map and the second distance map are generated in 620. In this case, the first distance map refers to an advantage weighted value to be applied to each pixel of the first area, and the second distance map refers to a penalty weighted value to be applied to each pixel of the second area. For example, the apparatus 100 for determining a lesion similarity may calculate the shortest distance between each pixel of the reference image and the boundary of the reference lesion area, and may generate the first distance map and the second distance map based on the calculation.

Subsequently, a similarity between the reference lesion area and the target lesion area may be calculated in 630 by applying the advantage weighted value to a binary value of each pixel of the first area based on the first distance map, and by applying the penalty weighted value to a binary value of each pixel of the second area based on the second distance map. For example, the apparatus 100 for determining a lesion similarity may calculate a similarity between the reference lesion area and the target lesion area by using Equation 1.

The present disclosure can be realized as a computer-readable code written on a computer-readable recording medium. Codes and code segments needed for realizing the present disclosure can be easily deduced by computer programmers of ordinary skill in the art. The computer-readable recording medium may be any type of recording device in which data is stored in a computer-readable manner Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A computer program product comprising a non-transitory computer-readable storage medium configured to store a computer readable program comprising instructions configured to, when executed by a computing device, cause the computing device to:
   receive input of a reference image including a reference lesion area, and a target image including a target lesion area;
   divide the target lesion area to a first area overlapped with the reference lesion area and a second area not overlapped with the reference lesion area;
   determine a similarity between the reference lesion area and the target lesion area by at least one of:
      applying an advantage weighted value to a pixel included in the first area of the target lesion area, the advantage weighted value increasing as the pixel of the first area gets closer to a center of the reference lesion area, or
      applying a penalty weighted value to a pixel included in the second area of the target lesion area, the penalty weighted value increasing as the pixel of the second area gets farther from the reference lesion area;

modify a lesion segmentation algorithm, that has detected the target lesion area from the target image, based on a result of the similarity determination to improve an accuracy of the lesion segmentation algorithm; and identify the target lesion area from the target image via the modified lesion segmentation algorithm.

2. The computer program product of claim 1, wherein the reference lesion area is detected by a user, and wherein the target lesion area is detected by a lesion segmentation algorithm.

3. The computer program product of claim 1, wherein the advantage weighted value and the penalty weighted value are increased linearly or exponentially.

4. The computer program product of claim 1, wherein the instructions further cause the computing device to:
calculate the shortest distance between each pixel of the reference image and a boundary of the reference lesion area,
generate a first distance map representing the advantage weighted value and a second distance map representing the penalty weighted value based on the calculated shortest distance, and
calculate the similarity between the reference lesion area and the target lesion area by using the first distance map and the second distance map.

5. The computer program product of claim 4, wherein the instructions further cause the computing device to:
binarize the reference image and the target image.

6. The computer program product of claim 5, wherein the instructions further cause the computing device to:
binarize the reference image so that each pixel inside the reference lesion area is binarized to a binary value "1", and each pixel outside the reference lesion area is binarized to a binary value "0", and
binarize the target image so that each pixel inside the target lesion area is binarized to a binary value "1", and each pixel outside the target lesion area is binarized to a binary value "0".

7. The computer program product of claim 5, wherein the instructions further cause the computing device to:
calculate the similarity between the reference lesion area and the target lesion area by using $$sim = \frac{sum(DM1. * (A \& B))}{sum(DM1) + sum(DM2. * (A|B))},$$

wherein A indicates a matrix representing a binarized reference image, B indicates a matrix representing a binarized target image, DM1 indicates a matrix representing the first distance map, and DM2 indicates a matrix representing the second distance map.

8. A method of determining a lesion similarity, the method comprising:
receiving input of a reference image including a reference lesion area, and a target image including a target lesion area;
dividing the target lesion area to a first area overlapped with the reference lesion area, and a second area not overlapped with the reference lesion area;
determining a similarity between the reference lesion area and the target lesion area by at least one of:

applying an advantage weighted value to a pixel included in the first area of the target lesion area, the advantage weighted value increasing as the pixel of the first area gets closer to a center of the reference lesion area, or applying a penalty weighted value to a pixel included in the second area of the target lesion area, the penalty weighted value increasing as the pixel of the second area gets farther from the reference lesion area;

modifying a lesion segmentation algorithm, that has detected the target lesion area from the target image, based on a result of the similarity determination to improve an accuracy of the lesion segmentation algorithm; and identifying the target lesion area from the target image via the modified lesion segmentation algorithm.

9. The method of claim 8, wherein the reference lesion area is detected by a user, and wherein the target lesion area is detected by a lesion segmentation algorithm.

10. The method of claim 8, wherein the advantage weighted value and the penalty weighted value are increased linearly or exponentially.

11. The method of claim 8, wherein the determining of the similarity comprises:
calculating the shortest distance between each pixel of the reference image and a boundary of the reference lesion area;
generating a first distance map representing the advantage weighted value and a second distance map representing the penalty weighted value based on the calculated shortest distance; and
calculating the similarity between the reference lesion area and the target lesion area by using the first distance map and the second distance map.

12. The method of claim 11, wherein the determining of the similarity further comprises binarizing the reference image and the target image.

13. The method of claim 12, wherein the binarizing comprises:
binarizing the reference image so that each pixel inside the reference lesion area is binarized to a binary value "1", and each pixel outside the reference lesion area is binarized to a binary value "0"; and
binarizing the target image so that each pixel inside the target lesion area is binarized to a binary value "1", and each pixel outside the target lesion area is binarized to a binary value "0".

14. The method of claim 12, wherein the calculating of the similarity comprises calculating the similarity between the reference lesion area and the target lesion area by using $$sim = \frac{sum(DM1. * (A \& B))}{sum(DM1) + sum(DM2. * (A|B))},$$

wherein A indicates a matrix representing a binarized reference image, B indicates a matrix representing a binarized target image, DM1 indicates a matrix representing the first distance map, and DM2 indicates a matrix representing the second distance map.

15. The computer program product of claim 1, wherein the instructions are distributed over at least one network coupled computer system.

16. A computer program product comprising a non-transitory computer-readable storage medium configured to store a computer readable program comprising instructions configured to, when executed by a computing device, cause the computing device to:
- receive input of a medical image including a reference lesion area and a target lesion area;
- divide the target lesion area to a first area overlapped with the reference lesion area, and a second area not overlapped with the reference lesion area;
- determine a similarity between the reference lesion area and the target lesion area by at least one of:
  - applying an advantage weighted value to a pixel included in the first area of the target lesion area, the advantage weighted value increasing as the pixel of the first area gets closer to a center of the reference lesion area, or
  - applying a penalty weighted value to a pixel included in the second area of the target lesion area, the penalty weighted value increasing as the pixel of the second area gets farther from the reference lesion area;
- modify a lesion segmentation algorithm, that has detected the target lesion area from the target image, based on a result of the similarity determination to improve an accuracy of the lesion segmentation algorithm; and
- identify the target lesion area from the target image via the modified lesion segmentation algorithm.

17. The computer program product of claim 16, wherein the reference lesion area is detected by a user, and wherein the target lesion area is detected by a lesion segmentation algorithm.

* * * * *